United States Patent [19]
Prakash et al.

[11] Patent Number: 6,077,962
[45] Date of Patent: Jun. 20, 2000

[54] N-3, 3-DIMETHYLBUTYL-L-ASPARTIC ACID AND ESTERS THEREOF, THE PROCESS OF PREPARING THE SAME, AND THE PROCESS FOR PREPARING N-(N-(3,3-DIMETHYLBUTYL) -α L-ASPARTYL)-L-PHENYLALANINE 1-METHYL ESTER THEREFROM

[75] Inventors: Indra Prakash, Hoffman Estates; Marie-Christine D. Chapeau, Chicago, both of Ill.

[73] Assignee: The NutraSweet Company, Chicago, Ill.

[21] Appl. No.: 09/219,898

[22] Filed: Dec. 24, 1998

[51] Int. Cl.[7] ........................ C07D 307/34; C07C 229/28
[52] U.S. Cl. .............................. 549/253; 560/24; 560/41; 562/568; 562/571
[58] Field of Search ........................ 560/41, 24; 562/571, 562/568; 549/253

[56] References Cited

U.S. PATENT DOCUMENTS 5,480,668   1/1996   Nofre et al. ............................ 426/548
5,510,508   4/1996   Claude et al. ............................ 560/41
5,728,862   3/1998   Prakash ..................................... 560/40

OTHER PUBLICATIONS

Database CAOLD on STN, Acc. No. CA55:189d, Greenhalgh, 'Color Couplers', Brit. 830,797 (abstract), 1961.

*Primary Examiner*—Gary Geist
*Assistant Examiner*—Brian J. Davis
*Attorney, Agent, or Firm*—Fitzpatrick, Cella, Harper & Scinto

[57] ABSTRACT

This invention relates to the chemical synthesis of N-[N-(3,3-dimethylbutyl)-L-α-aspartyl]-L-phenylalanine 1-methyl ester using peptide coupling methods. The coupling reaction is conducted by condensation of an activated derivative of novel N-neohexyl-L-aspartic acid with L-phenylalanine or L-phenylalanine methyl ester or by enzymatic coupling of N-neohexyl-L-aspartic acid with L-phenylalanine or L-phenylalanine methyl ester. This invention also relates to novel N-(3,3-dimethylbutyl)-L-aspartic acid, derivatives thereof and the preparation thereof. The activated derivative of N-neohexyl-L-aspartic acid may be an anhydride, mixed anhydride, active ester or an intermediate activated derivative thereof.

29 Claims, No Drawings

N-3, 3-DIMETHYLBUTYL-L-ASPARTIC ACID AND ESTERS THEREOF, THE PROCESS OF PREPARING THE SAME, AND THE PROCESS FOR PREPARING N-(N-(3,3-DIMETHYLBUTYL) -α L-ASPARTYL)-L-PHENYLALANINE 1-METHYL ESTER THEREFROM

BACKGROUND OF THE INVENTION

1. Field of the Invention

This invention relates to N-3,3-dimethylbutyl-L-aspartic acid and derivatives thereof. The invention also relates to a process for preparing N-[N-(3,3-dimethylbutyl)-L-α-aspartyl]-L-phenylalanine 1-methyl ester (neotame) via peptide coupling of a derivative of the novel N-(3,3-dimethylbutyl) L-aspartic acid with L-phenylalanine or an L-phenylalanine ester.

2. Related Background Art

N-[N-(3,3-dimethylbutyl)-L-α-aspartyl]-L-phenylalanine 1-methyl ester (neotame) is a highly intense non-nutritive sweetening agent useful to impart sweetness to a wide variety of food products. This sweetener, disclosed in U.S. Pat. No. 5,480,668, is approximately 8,000 times as sweet as sucrose, on a weight basis. Thus, very small quantities of this sweetening agent may be used to produce foods and food products that are equi-sweet tasting to presently available high caloric food products.

U.S. Pat. No. 5,510,508 describes a method for preparing N-[N-(3,3-dimethylbutyl)-L-α-aspartyl]-L-phenylalanine 1-methyl ester of the formula

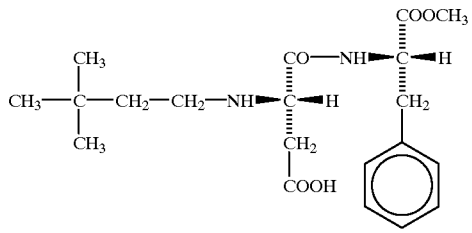

comprising treating an aqueous acetic acid/alcoholic solution of aspartame and 3,3-dimethylbutyraldehyde, at room temperature, with hydrogen at a pressure less than or equal to 1 bar (0.1 MPa) in the presence of a catalyst based on platinum or palladium. The product is purified by precipitation and filtration after the alcohol is removed from the solution under vacuum.

U.S. Pat. No. 5,728,862 describes a method comprising treating a solution of aspartame and 3,3-dimethylbutyraldehyde in an organic solvent with the reducing agent, hydrogen in the presence of a catalyst. After removal of the catalyst, water is added to form an aqueous/organic solvent solution containing about 17% to about 30% of the organic solvent, by weight, from which the neotame is obtained by precipitation and filtration.

It would be desirable, however, to develop more efficient and cost-effective methods of preparing high-purity neotame from readily available or readily obtainable materials.

SUMMARY OF THE INVENTION

This invention relates to novel N-(3,3-dimethylbutyl)-L-aspartic acid and derivatives thereof, e.g., esters, anhydrides and the like. These novel aspartic compounds may be prepared by reductive alkylation of 3,3-dimethylbutyraldehyde with L-aspartic acid or derivatives thereof. N-(3,3-Dimethylbutyl)-L-aspartic acid may also be prepared by reductive alkylation of 3,3-dimethylbutyraldehyde with L-aspartic acid dialkyl ester, followed by hydrolysis of the dialkyl ester moieties.

This invention also relates to processes for the preparation of N-[N-(3,3-dimethylbutyl)-L-α-aspartyl]-L-phenylalanine 1-methyl ester using peptide coupling methodology. In these processes, the peptide amide bond of N-[N-(3,3-dimethylbutyl)-L-α-aspartyl]-L-phenylalanine 1-methyl ester may be formed via peptide coupling of an activated derivative of N-(3,3-dimethylbutyl)-L-aspartic acid with L-phenylalanine or an L-phenylalanine ester. High purity N-[N-(3,3-dimethylbutyl)-L-α-aspartyl]-L-phenylalanine 1-methyl ester may be obtained by direct crystallization of the condensed product or by additional functional group transformation of that product, followed by crystallization or by column chromatography.

DETAILED DESCRIPTION OF THE INVENTION

This invention is directed to novel N-(3,3-dimethylbutyl)-L-aspartic acid and derivatives thereof represented by the formula

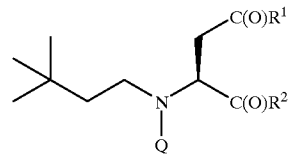

wherein $R^1$ and $R^2$ are independently hydroxy or lower alkoxy having 1 to 6 carbon atoms or together are oxygen, forming an anhydride; and Q is hydrogen or $(CH_3)_3C(CH_2)_2-$. Preferably Q is hydrogen. Preferably $R^1$ and $R^2$ are hydroxy or methoxy.

This invention is also directed to useful methods for the preparation of N-[N-(3,3-dimethylbutyl)-L-α-aspartyl]-L-phenylalanine 1-methyl ester in high yield and in high purity via peptide coupling of activated derivatives of the novel N-(3,3-dimethylbutyl)-L-aspartic acid with L-phenylalanine, or the methyl ester thereof.

Scheme I illustrates a method of preparation of N-(3,3-dimethylbutyl)-L-aspartic acid via reductive alkylation of L-aspartic acid using 3,3-dimethylbutyraldehyde.

SCHEME I

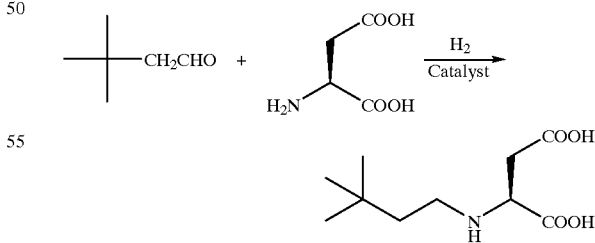

The reductive alkylation reaction is typically conducted in water, a lower alkyl alcohol solvent, or mixtures thereof. Lower alkyl alcohol solvents, e.g., methanol, ethanol, propanol, isopropanol, butanol, and the like, are preferred. The reduction is typically conducted using palladium on carbon in a hydrogen atmosphere. Other hydrogenation catalysts which may be used include platinum on carbon, platinum black, palladium black, nickel on silica and alumina homogeneous hydrogenation catalysts, Raney nickel, ruthenium black, ruthenium on carbon, palladium oxide, palladium hydroxide on carbon, rhodium black, rhodium on carbon or alumina. Other useful reducing agents include sodium cyanoborohydride, lithium or sodium borohydride. Addition of a base, e.g., sodium bicarbonate, sodium carbonate, potassium bicarbonate, potassium carbonate, lithium carbonate or an organic base, is optionally used to solubilize the aspartic acid. If the reaction is conducted in the absence of a base, dialklyation occurs and N,N-di-(3,3-dimethylbutyl)-L-aspartic acid may be obtained.

Alternatively, as illustrated in Scheme II, N-(3,3-dimethylbutyl)-L-aspartic acid may be obtained via a two step process of reductive alkylation of a di-protected L-aspartic acid with 3,3-dimethylbutyraldehyde followed by removal of the carboxyl protecting groups. Each of the carboxyl groups of L-aspartic acid are protected with a suitable protecting group. Carboxyl-protecting groups that are suitable for use in the present invention are those that are both stable to the reductive alkylation reaction conditions and that can be removed from the final product without racemization or degradation of that product. Optionally the carboxyl groups are protected by conversion into ester moieties. Exemplary ester groups include $C_1$–$C_4$ alkyl esters, substituted $C_1$–$C_4$ alkyl esters, silyl esters and the like. Methods of protecting and de-protecting carboxyl-containing compounds are well known to those skilled in the art and are described in T. W. Greene, et al., "Protective Groups in Organic Synthesis" Second Edition, John Wiley & Sons, New York, N.Y. (1991). In this reaction sequence, the reductive alkylation may be conducted in same manner without the addition of a base, and using the same hydrogenation catalysts or reducing agents as described above. The reaction may also be conducted in organic solvents such as ethyl acetate, propyl acetate, isopropyl acetate, butyl acetate, tetrahydrofuran (THF), diethyl ether, tert-butylmethyl ether, toluene and the like.

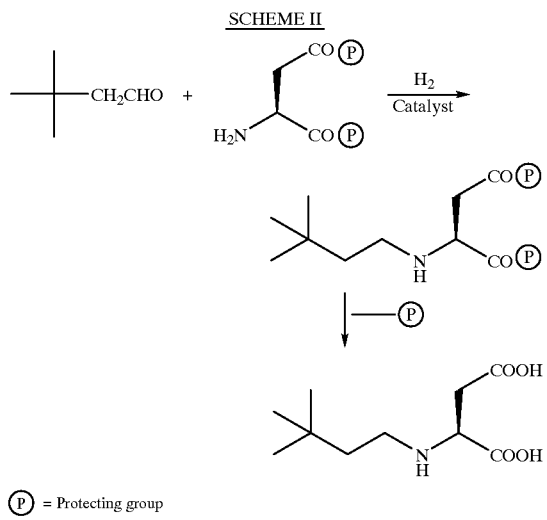

As previously noted, yet another embodiment of this invention is directed to methods of preparing N-[N-(3,3-dimethylbutyl)-L-α-aspartyl]-L-phenylalanine 1-methyl ester via peptide coupling of an activated derivative of N-(3,3-dimethylbutyl)-L-aspartic acid with L-phenylalanine or an L-phenylalanine ester. According to the present invention, an activated derivative of N-(3,3-dimethylbutyl)-L-aspartic acid includes the anhydride or mixed anhydrides of the aspartic acid as well as intermediate activated derivatives, which may or may not be isolated, formed by treatment of the aspartic acid, or a protected aspartic acid, with a peptide coupling agent. Methods of peptide coupling are well known to those skilled in the art and are described in M. Bodansky, et al., "The Practice of Peptide Synthesis, Reactivity and Structure, Concepts in Organic Chemistry," Volume 21, Second, Revised Edition, Springer-Verlag, New York, N.Y. (1994).

In a first embodiment of the peptide coupling method of this invention, the peptide amide bond of N-[N-(3,3-dimethylbutyl)-L-α-aspartyl]-L-phenylalanine 1-methyl ester is formed via condensation of L-phenylalanine or L-phenylalanine methyl ester with the anhydride of N-(3,3-dimethylbutyl)-L-aspartic acid, hereinafter N-neohexyl-L-aspartic anhydride. Scheme III illustrates the preparation of N-neohexyl-L-aspartic anhydride and Scheme IV illustrates the preparation of N-[N-(3,3-dimethylbutyl)-L-α-aspartyl]-L-phenylalanine 1-methyl ester via this first embodiment. In the structures in the following Schemes III to VII, the N-(3,3-dimethylbutyl), or neohexyl, moiety is abbreviated "Neo".

SCHEME III

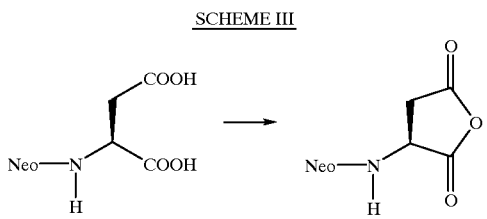

N-Neohexyl-L-aspartic anhydride may be prepared by dehydration of N-neohexyl-L-aspartic acid using a dehydrating agent. Dehydration reactions are known to those skilled in the art and may be accomplished using known reaction conditions. Exemplary dehydrating agents include phosphorus pentoxide, phosphorous trichloride, phosphoric acid, acid anhydrides, such as acetic anhydride and formic anhydride, carbodiimides, such as dicyclohexyl carbodiimide (DCC), and the like.

Optionally, prior to formation of the anhydride, the amino group of N-neohexyl-L-aspartic acid may be protected by forming an N-protected-N-neohexyl-L-aspartic acid. Amino-protecting groups that are suitable for use in this invention must be stable to the dehydration reaction conditions and must be removable from the N-neohexyl-L-α-aspartyl-L-phenylalanine or its methyl ester without racemization. Suitable amino-protecting groups are generally carbamate or amide type protecting groups. Exemplary amino-protecting groups, include formyl, acetyl, benzyloxycarbonyl, tert-butoxycarbonyl and p-methoxybenzyloxycarbonyl. Methods for protecting and deprotecting nitrogen-containing compounds using these groups are well known to those skilled in the art and are described in T. W. Greene, et al., supra.

Preferably, the nitrogen protecting group is either benzyloxycarbonyl, formyl, or acetyl and more preferably formyl. N-Benzyloxycarbonyl-N-neohexyl-L-aspartic acid may be formed by reaction of N-neohexyl-L-aspartic acid with benzyl chloroformate. N-Formyl-N-neohexyl-L-aspartic acid may be prepared by reaction of N-neohexyl-L-aspartic acid with a formylating agent such as formic anhydride or formic acid and acetic anhydride. N-Acetyl-N-neohexyl-L-aspartic acid may be prepared by reaction of N-neohexyl-L-aspartic acid with an acetylating agent such as acetic anhydride. Advantageously, in the present invention, use of formic anhydride or acetic anhydride, as the dehydrating agent, in the presence of an acid such as formic acid or phosphoric acid, provides for formation of N-neohexyl-L-aspartic anhydride from either N-neohexyl-L-aspartic acid or an N-protected-N-neohexyl-L-aspartic acid.

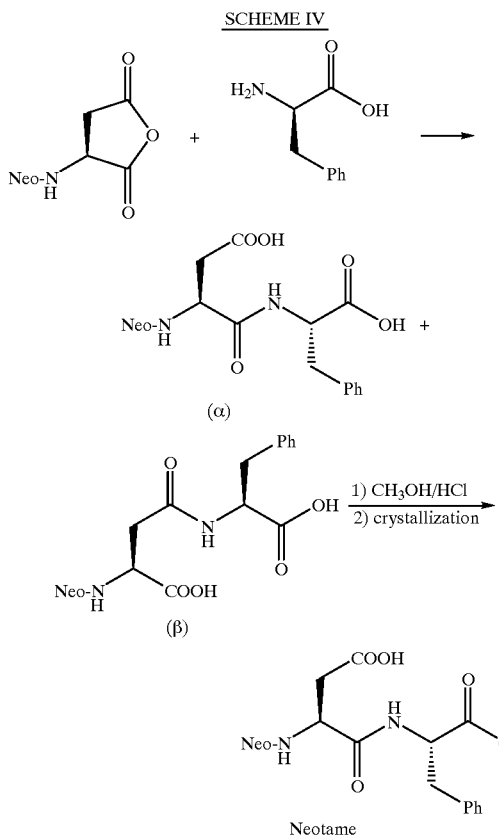

Formation of the peptide amide bond of N-[N-(3,3-dimethylbutyl)-L-α-aspartyl]-L-phenylalanine 1-methyl ester may be accomplished by condensation of N-neohexyl-L-aspartic anhydride with L-phenylalanine, as illustrated in Scheme IV. Amide bond formation occurs by reacting equimolar amounts of the aspartic anhydride and phenylalanine in an inert solvent. The reaction may be conducted at about 20–100° C. Exemplary inert solvents, suitable for use in the amide-bond forming reaction, include toluene, methyl acetate, ethyl acetate, tetrahydrofuran, acetonitrile, dioxane and dimethylformamide (DMF) containing either organic acids, such as acetic acid, propionic acid, butyric acid, isobutyric acid, or no acids.

The condensation reaction of N-neo-L-aspartic anhydride with L-phenylalanine produces a mixture of two amide products, N-neohexyl-α-L-aspartyl-L-phenylalanine and N-neohexyl-β-L-aspartyl-L-phenylalanine. N-Neo-L-aspartic anhydride is an unsymmetrical anhydride; that is, the aspartic anhydride, and the precursor aspartic acid, contain two different carboxyl groups designated α and β, based on their relationship to the nitrogen moiety. The α- and β-amide products are formed by reaction of phenylalanine with either the α-carboxyl or the β-carboxyl group of the anhydride.

Both α- and β-aspartic acid amides are obtained from the condensation of N-neohexyl-L-aspartic anhydride L-phenylalanine. The ratio of isomers obtained in this condensation reaction is generally about 2:1 to about 3:1.

Esterification of the mixture of α- and β-aspartic acid amides with methanol, in acid, forms a mixture of the α and β product. The desired N-[N-(3,3-dimethylbutyl)-L-α-aspartyl]-L-phenylalanine 1-methyl ester may be isolated in pure form by crystallization or column chromatography of this mixture. Use of methanol and water, such as described, for example, in U.S. Pat. No. 5,728,862, the disclosure of which is incorporated by reference herein, provides excellent recovery of high purity alpha product.

Alternatively, N-[N-(3,3-dimethylbutyl)-L-α-aspartyl]-L-phenylalanine 1-methyl ester may be formed directly using the peptide coupling method of the present invention via condensation of N-neohexyl-L-aspartic anhydride with L-phenylalanine methyl ester, as illustrated in Scheme V.

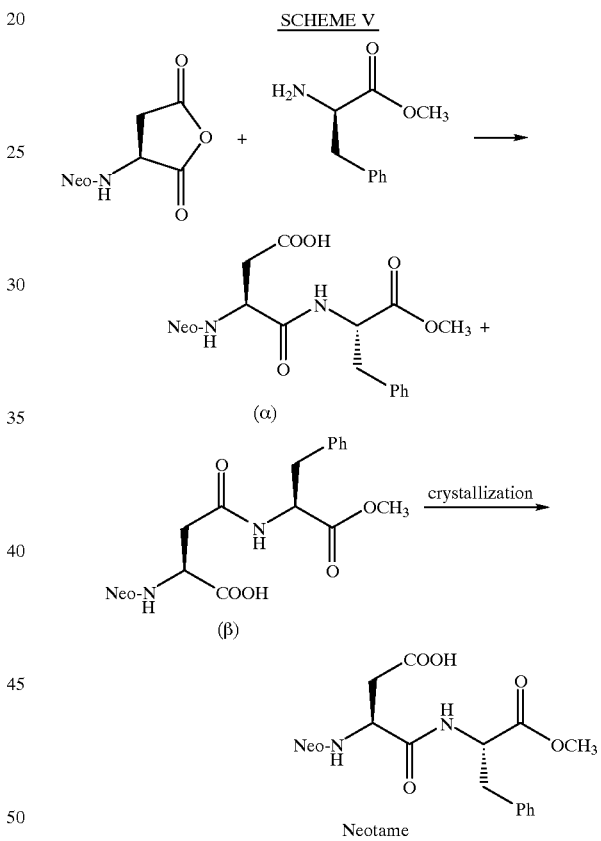

The peptide coupling reaction may be conducted under the same conditions useful for coupling L-phenylalanine, described above. This coupling reaction forms a mixture of N-[N-(3,3-dimethylbutyl)-L-α-aspartyl]-L-phenylalanine 1-methyl ester and N-[N-(3,3-dimethylbutyl)-L-β-aspartyl]-L-phenylalanine 1-methyl ester, generally, in a ratio of about 2:1 to about 3:1. The N-[N-(3,3-dimethylbutyl)-L-α-aspartyl]-L-phenylalanine 1-methyl ester may be obtained in high purity by recrystallization of the neotame mixture using methanol and water or by column chromatography using silica gel or resins.

Scheme VI illustrates yet another embodiment of the peptide coupling method of this invention for the preparation of N-[N-(3,3-dimethylbutyl)-L-α-aspartyl]-L-phenylalanine 1-methyl ester.

Scheme VI

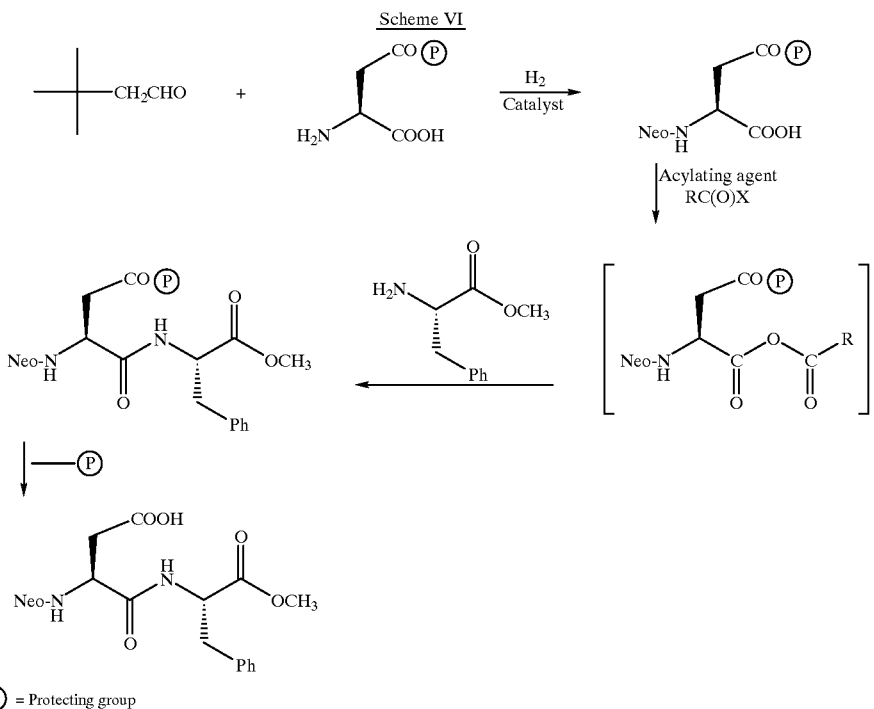

Ⓟ = Protecting group

In this embodiment, formation of the peptide amide bond of N-[N-(3,3-dimethylbutyl)-L-α-aspartyl]-L-phenylalanine 1-methyl ester is accomplished by condensation of L-phenylalanine methyl ester with a mixed anhydride of N-neohexyl-L-aspartic acid. A mixed anhydride is an anhydride derived from two different carboxylic acid-containing compounds, or may be formed in situ from a carboxylic acid-containing compound and a phosphoric acid derivative, such as o-phenylene phosphochloridite. A special category of mixed anhydrides is the N-carboxy- or Leuch's anhydrides, prepared by treatment of an amino acid, e.g., the β-protected aspartic acid, with phosgene, or by heating benzyloxycarbonyl amino acid chlorides. These mixed anhydrides may be obtained in high efficiency using methods well known in the art.

The mixed anhydride of N-neohexyl-L-aspartic acid is preferably prepared by reaction of the aspartic acid with an acylating reagent, such as an alkyl or aryl acid chloride, chloroformate, chlorocarbonate or imide. The reaction is typically conducted in the presence of a non-nucleophilic base at ambient or reduced temperature. Exemplary non-nucleophilic bases include, alkali carbonates, such as sodium carbonate, alkyl amines, such as tertiary amines, triethylamine or N-methyl morpholine, aromatic amines, such as pyridine, and the like. The reaction may be conducted in a solvent, such as toluene, DMF, acetonitrile, methyl acetate, dioxane and the like. Alternatively, amine bases, e.g., triethylamine or pyridine, may also be used as suitable reaction solvents. Exemplary acylating reagents include but are not limited to acid chlorides such as pivaloyl chloride, isovaleryl chloride, benzoyl chloride, p-nitrobenzoyl chloride, pentachlorobenzoyl chloride, pentafluorobenzoyl chloride and the like, chloroformates, such as tertiary butyl chloroformate, isopropyl chloroformate, isobutyl chloroformate, and the like, chlorocarbonates, such as isobutyl chlorocarbonate, ethyl chlorocarbonate and the like, or imides such as N-hydroxy succinimide, N-hydroxysuccinimide and the like.

As indicated above, N-neohexyl-L-aspartic acid contains two different carboxyl groups, α- and β-, and either of these carboxyl groups may participate in the reaction to form the mixed anhydride. Accordingly, one of the carboxyl groups, the β-carboxyl, is optionally protected so that formation of the mixed anhydride, and eventual formation of the peptide amide bond, occurs selectively at the α-carboxyl group. The β-carboxyl group may be protected with any suitable carboxyl-protecting group that is not reactive in either the anhydride forming reaction or the peptide coupling reaction and can be removed from the final product, N-[N-(3,3-dimethylbutyl)-L-α-aspartyl]-L-phenylalanine 1-methyl ester, without racemization or degradation of that product. Optionally, the β-carboxyl group is protected by conversion into an ester moiety. Exemplary ester groups, include tert-butyl ester, silyl ester, benzyl esters. Methods of protecting and deprotecting carboxyl-containing compounds are well known to those skilled in the art and are described in T. W. Greene, et al., supra.

The β-carboxyl group of N-neohexyl-L-aspartic acid is protected at a step prior to the anhydride-forming reaction. Optionally, the β-carboxyl group is protected at a step prior to formation of N-neohexyl-L-aspartic acid by reductive alkylation. β-Carboxylic esters may also be formed by the reaction of N-neohexyl-L-aspartic anhydride with an alcohol. Scheme VI illustrates the preparation of a β-protected N-neohexyl-L-aspartic acid, via reductive alkylation of a β-protected L-aspartic acid with 3,3-dimethylbutyraldehyde. The reductive alkylation reaction may be performed using conditions and reagents, as described above. The β-protected N-neohexyl-L-aspartic acid, as prepared according to the method of Scheme VI, may be treated with an acylating agent, according to the method of Scheme V, described above, to form a mixed anhydride (R is alkyl or aryl). Formation of the peptide amide bond may be accomplished by condensation of the mixed anhydride of the β-protected N-neohexyl-L-aspartate with L-phenylalanine methyl ester, using coupling conditions described above. N-[N-(3,3-dimethylbutyl)-L-α-aspartyl]-L-phenylalanine 1-methyl ester may be prepared by deprotection, that is, removal of the β-protecting group, from the resulting β-protected N-[N-(3,3-dimethylbutyl)-L-α-aspartyl]-L-phenylalanine 1-methyl ester using reaction conditions known in the art. If desired, the N-[N-(3,3-dimethylbutyl)-L-α-aspartyl]-L-phenylalanine 1-methyl ester may be further purified by crystallization from methanol/water or by column chromatography.

Scheme VII illustrates yet another embodiment of the peptide coupling method of this invention for the preparation of N-[N-(3,3-dimethylbutyl)-L-β-aspartyl]-L-phenylalanine 1-methyl ester.

Scheme VII

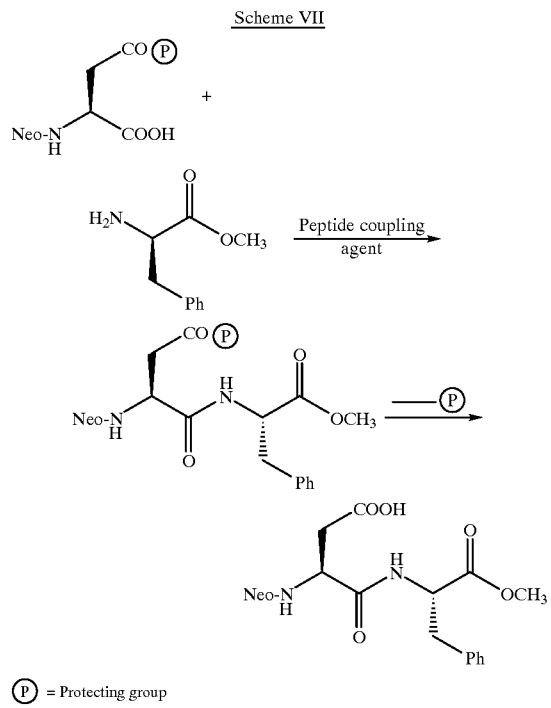

Ⓟ = Protecting group

In this embodiment, formation of the peptide amide bond of N-[N-(3,3-dimethylbutyl)-L-β-aspartyl]-L-phenylalanine 1-methyl ester is accomplished by direct condensation of an L-phenylalanine ester with an N-neohexyl-L-aspartic acid using a peptide coupling agent. Useful peptide coupling agents function to form an intermediate activated derivative of a carboxylic acid moiety of the N-neohexyl-L-aspartic acid. The intermediate activated aspartic acid derivative, which may or may not be isolated, undergoes reaction with the nitrogen moiety of L-phenylalanine 1-methyl ester to form the peptide amide bond of N-[N-(3,3-dimethylbutyl)-L-α-aspartyl]-L-phenylalanine 1-methyl ester. An example of an activated aspartic acid derivative that may be isolated is a β-protected aspartyl acid chloride, which undergoes peptide coupling via simple amide formation by reaction of the acid chloride and phenylalanine or phenylalanine methyl ester. Examples of other isolable activated derivatives include hydrazides and active esters. Hydrazide derivatives of β-protected aspartic acid may be formed using hydrazine hydrate or derivatized hydrazines according to conventional procedures. Coupling of β-protected aspartyl hydrazide derivatives may be accomplished by conversion of the hydrazide to the azide, followed by treatment with phenylalanine or phenylalanine methyl ester. Active ester derivatives of β-protected aspartic acid may be formed using conventional esterification techniques. Active ester derivatives useful in peptide coupling reactions include, but are not limited to, cyanomethyl esters, p-nitrophenyl esters, o-nitrophenyl esters, 2,4-dinitrophenyl esters, 2,4,5-trinitrophenyl esters, pentachlorophenyl esters, pentafluorophenyl esters, tert-butyloxycarbonylamino acid pentafluorophenyl esters, N-hydroxyphthalimide esters, N-hydroxysuccinimide esters, 1-hydroxypyridine esters, 5-chloro-8-hydroxy-quinoline esters, and the like. Coupling of active ester derivatives with phenyl alanine or phenylalanine methyl ester may be accomplished by simple reaction of the two materials under conventional acidic, neutral or basic reaction conditions. Alternatively, the active ester coupling reaction may be catalyzed using conventional coupling reagents, such as imidazole, 1-hydroxybenzotriazole, or 3-hydroxy-3,4-dihydro-quinazoline-4-one. Typically, the activated aspartic acid derivative is not isolated, but is formed under the reaction conditions as an intermediate product that participates in the formation of the peptide amide bond. The intermediate activated aspartic acid derivative is preferably prepared by reaction of a β-protected N-neohexyl-L-aspartic acid with a peptide coupling agent. The β-carboxyl group of the N-neohexyl L-aspartic acid may be protected with any suitable carboxyl-protecting group that is not reactive in the peptide coupling reaction and that can be removed from the final product, N-[N-(3,3-dimethylbutyl)-L-α-aspartyl]-L-phenylalanine 1-methyl ester, without racemization or degradation of that product. Suitable β-protected aspartic acids are described above. Peptide coupling agents that are useful in the method of the present invention include, but are not limited to dicyclohexyl carbodiimide (DCC), DCC/1-hydroxybenzotriazole, DCC/N-hydroxysuccinimide, 1-isobutoxycarbonyl-2-isobutoxy-1,2-dihydroquinone (IIDQ), carbonyldiimidizole, N-ethyl-5-phenylisoxazolium-3'-sulfonate (Woodward's Reagent K), benzotriazolyl-N-hydroxytris(dimethyamino)phosphonium hexafluorophosphate (BOP) and the like. The above-described peptide coupling agents and methods of using these agents, and others, may be found in any of several reviews on the subject, for example M. Bodansky, et al., supra.

In yet another embodiment of this invention, enzymatic methods may be used to form the peptide amide bond of N-[N-(3,3-dimethylbutyl)-L-α-aspartyl]-L-phenylalanine 1-methyl ester, as illustrated in Scheme VIII.

SCHEME VIII

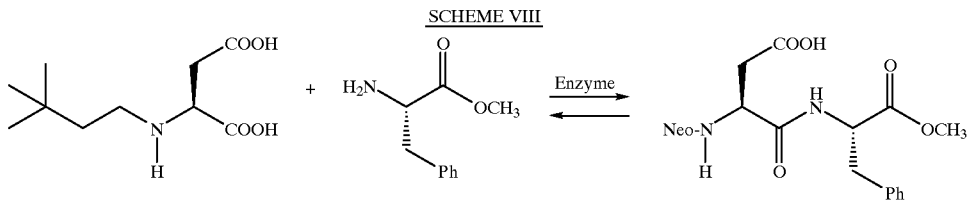

According to this embodiment, N-neohexyl-L-aspartic acid may be reacted with L-phenylalanine methyl ester, in the presence of the protease enzyme, papain, to provide α-neotame. The N-protected N-neohexyl-L-aspartic acid may also be used to form the peptide coupled product. Removal of the nitrogen protecting group provides the N-[N-(3,3-dimethylbutyl)-L-α-aspartyl]-L-phenylalanine 1-methyl ester. The solvent in which the reaction is conducted may be selected such that the desired product is insoluble, or only slightly soluble in the solvent, resulting in the a shift in the reaction equilibrium to favor formation of the peptide. Nitrogen protecting groups, useful in the enzymatic method of this invention may include any of the protecting groups discussed above. Preferably, acetoacetyl, acetyl, benzoyl, benzyloxycarbonyl, tert-butyloxycarbonyl, formyl, isovaleryl, (p-methoxybenzyl)oxycarbonyl, or phenylacetyl. Preferably, the nitrogen protecting group is benzyloxycarbonyl. Useful solvents in which the enzymatic coupling reaction may be conducted include those that are miscible or immiscible with water. Exemplary solvents include organic co-solvents such as glycerol and other glycols, acetonitrile, ethyl acetate, tert-amyl alcohol, and triethyl phosphate. Mixed solvent systems, such as ethyl acetate and tert-amyl alcohol may also be used.

After the coupling reaction has been completed using any of the above-described methods, any protecting groups that may have be present on the aspartic acid moiety (e.g., nitrogen protecting groups or the β-carboxyl protecting group) may be removed using typical de-protection procedures. The N-[N-(3,3-dimethylbutyl)-L-α-aspartyl]-L-phenylalanine 1-methyl ester may be further purified by crystallization from methanol/water or by column chromatography.

The examples which follow are intended as an illustration of certain preferred embodiments of the invention, and no limitation of the invention is implied.

EXAMPLE 1

N-Neohexyl-L-Aspartic acid

Process A

L-aspartic acid (4 g, 0.03 mol) was added to a Parr bottle containing a solution of sodium bicarbonate (5.04 g, 0.06 mol) in water (50 mL) to form a clear solution, with effervescence. A solution of 3,3-dimethylbutyraldehyde (3 g, 0.03 mol) in methanol (50 mL) was then added to the Parr bottle, followed by Pd/C (4% palladium on carbon, 50% wet, 0.4 g). The mixture was hydrogenated at 50 psi/room temperature for 2 days. If the reaction was not complete, fresh Pd/C (0.2 g) would be added and hydrogenation continued for an additional 8 hrs. The mixture was filtered through a Celite® bed, and the bed was washed with methanol (20 mL). The filtrate and washings were combined and concentrated under reduced pressure at 40–50° C. The pH of the remaining aqueous solution was adjusted to 3 with concentrated hydrochloric acid. The precipitated solid was filtered and dried in a vacuum oven at 50° C. for 4 hrs to give 4.75 g (73%) of crude N-neohexyl-L-aspartic acid. The crude product was slurried with aqueous ethanol (47.5, 80% ethanol, 20% water) for 15 minutes and filtered to give 3.3 g (51%) of >98% pure N-neohexyl-L-aspartic acid. M.P. 184–186° C.; $[\alpha]_D$ +12.35 (c=1, water); NMR ($D_2O$) δ3.37 (t, 3H); 2.25–2.65 (m, 4H); 1.27–1.47 (m, 2H); 0.89(s, 9H); Anal. Calc'd. for $C_{10}H_{19}NO_4$; C, 55.28; H, 8.81; N, 6.45; Found: C, 55.35; H, 8.86; N, 6.50.

EXAMPLE 2

N-Neohexyl-L-Aspartic acid Hydrochloride

Process B

Sodium hydrogen carbonate (1.68 g, 0.02 mol) was added to a Parr bottle containing a solution of dimethyl L-aspartate hydrochloride (3.94 g, 0.02 mol) in water (10 mL), followed by addition of 3,3-dimethylbutyraldehyde (2.2 g, 0.02 mol) in methanol (100 mL) and Pd/C (4% palladium on carbon, 50% wet), 10% by weight of substrate. The mixture was hydrogenated at 50 psi at room temperature for 1.5 hrs then filtered through a Celite® bed and the bed washed with methanol (10 mL). The filtrate and washings were concentrated under reduced pressure. The residual aqueous solution was extracted with diethyl ether (2×100 mL). The organic layer was washed with aqueous saturated sodium hydrogen carbonate solution (50 mL), dried over anhydrous magnesium sulfate, filtered and concentrated to give N-neohexyl-L-aspartic acid dimethyl ester (4.65 g, 95%) as an oil. NMR ($CDCl_3$) δ3.67 (s, 3H); 3.50 (s, 3H); 3.57(t, 3H); 2.37–2.70 (m, 4H); 1.20–1.40 (m, 2H); 0.80 (s, 9H).

A mixture of N-neohexyl-L-aspartic acid dimethyl ester (15 g, 0.061 mol) in 1N hydrochloric acid (350 mL) was heated at reflux for 4 hours to form a clear solution. The mixture was freeze dried to give N-neohexyl-L-aspartic acid hydrochloride as a white solid (14 g, 91%), M.P. 133–138° C., $[\alpha]_D$ +14.69 (c=1, water). Anal. Calc'd. for $C_{10}H_{19}NO_4$—HCl; C, 47.52; H, 7.92; N, 5.54; Cl, 14.05. Found: C, 47.84; H, 8.14; N, 5.31; Cl, 13.08.

EXAMPLE 3

N,N-Di-neohexyl L-Aspartic Acid

To a slurry of L-aspartic acid (4 g, 0.03 mol) in 1:1 methanol/water (80 mL) was added neat 3,3- dimethylbutyraldehyde (3 g, 0.03 mol), followed by Pd/C (4%, 50% wet, 0.5 g). The mixture was hydrogenated using $H_2$ (50 psi) at room temperature for 2 days. The resulting reaction mixture was filtered through a Celite® bed, and the bed washed with methanol (50 mL) The filtrate and washings were combined and the methanol removed using a rotary evaporator under reduced pressure at 40–50° C. to provide the N,N-di-neohexyl L-aspartic acid as a solid precipitate in water. The solid was filtered, washed with water (2 mL) and dried in a vacuum oven at 50° C. for 4 hrs to provide 3.2 g of N,N-di-neohexyl L-aspartic acid (36%), M.P. 197–198° C., $[\alpha]_D$ −3 (c=1, methanol). Anal. Calc'd. for $C_{16}H_{31}NO_4$; C, 63.78; H, 10.29; N, 4.65. Found: C, 63.43; H, 10.29; N, 4.70

EXAMPLE 4

N-Neohexyl-L-Aspartic Anhydride

Process A

Phosphorous trichloride (3.7 ml, 43 mmol) was added, dropwise, to a 10° C. slurry of N-neohexyl-L-aspartic acid (11.6 g, 53.4 mmol) in glacial acetic acid (50 ml). After addition was complete (0.5 hr), the resulting clear solution was stirred at room temperature overnight. The resulting solid precipitate was collected by vacuum filtration, washed with acetic acid and methylene chloride, then dried at 35–40° C. for 3 hours to give 3.62 g (69.8%) of pure N-neohexyl-L-aspartic anhydride.

EXAMPLE 5

N-Neohexyl-L-Aspartic Anhydride

Process B

N-Neohexyl-L-aspartic acid hydrochloride is dissolved in an aqueous solution of sodium bicarbonate with stirring. The solution is cooled, and treated with benzyloxycarbonyl chloride and aqueous sodium hydroxide, added in portions, alternatingly, with vigorous stirring. The resulting reaction mixture is stirred at room temperature for about 3 hours. The solution is extracted twice with diethyl ether and acidified to the Congo blue endpoint with concentrated hydrochloric acid. The N-benzyloxycarbonyl-N-neo-hexyl-L-aspartic acid separates as a solid or an oil that slowly solidifies. The acidified reaction mixture is cooled at 10–15° C. for several hours and the resulting solid is collected by filtration, is washed with water and is dried under vacuum. The N-benzyloxycarbonyl-N-neo-hexyl-L-aspartic acid may be used as recovered or may be recrystallized from a suitable solvent.

A solution of N-benzyloxycarbonyl-N-neohexyl-L-aspartic acid, in acetic anhydride with a catalytic amount of phosphoric acid, is heated at reflux for 0.5 to 5 hours, is cooled to room temperature, and is concentrated under reduced pressure, with heating. The residual material is dissolved in water, then neutralized with aqueous sodium hydroxide. The resulting precipitate is collected by vacuum filtration, and is recrystallized to provide substantially pure N-neohexyl-L-aspartic anhydride.

EXAMPLE 6

N-Neohexyl-α-Aspartame

Process A

N-Neohexyl-L-aspartic anhydride and L-phenylalanine are added to dry dioxane and the solution is stirred at 20–80° C. for 1–8 hours. The resulting reaction mixture is diluted with an organic solvent that is not miscible with water, washed successively with aqueous $KHCO_3$, then aqueous HCl, dried over anhydrous $Na_2SO_4$ and evaporated to dryness under reduced pressure, providing a mixture of amides: N-neohexyl-α-L-aspartyl-L-phenylalanine and N-neohexyl-β-L-aspartyl-L-phenylalanine. The amide mixture is dissolved in a methanol/hydrochloric acid solution and the resulting reaction mixture is stirred at 20–80° C. for 1–8 hours to form a mixture of N-[N-(3,3-dimethylbutyl)-L-α-aspartyl]-L-phenylalanine 1-methyl ester and N-[N-(3,3-dimethylbutyl)-L-β-aspartyl]-L-phenylalanine 1-methyl ester. Recrystallization of the (α- and β-aspartame mixture from methanol/water or column chromatography on silica gel using ethyl acetate:methanol:hexane (60:30:10) as an eluent provides pure N-[N-(3,3-dimethylbutyl)-L-α-aspartyl]-L-phenylalanine 1-methyl ester.

EXAMPLE 7

N-[N-(3,3-dimethylbutyl)-L-α-aspartyl]-L-phenylalanine 1-methyl ester

Process B

A mixture of N-neohexyl-L-aspartic anhydride hydrochloride (2 g, 8.5 mmol) and L-phenylalanine methyl ester in dry toluene (13 ml) was heated at 55–60° C. for about 3 hours, cooled to room temperature, and allowed to stand overnight. The resulting reaction mixture was concentrated to dryness under reduced pressure at 40–45° C. The residual solid material was dissolved in ethyl acetate (20 mL), washed successively with water (10 mL), aqueous $KHCO_3$, and aqueous HCl, dried over anhydrous $Na_2SO_4$ and evaporated to dryness under reduced pressure to provide a mixture of N-[N-(3,3-dimethylbutyl)-L-α-aspartyl]-L-phenylalanine 1-methyl ester and N-[N-(3,3-dimethylbutyl)-L-β-aspartyl]-L-phenylalanine 1-methyl ester (3 g). Recrystallization of the α- and β-aspartame mixture from methanol/water or column chromatography on silica gel using ethyl acetate:methanol:hexane (60:30:10) as an eluent provides pure N-[N-(3,3-dimethylbutyl)-L-α-aspartyl]-L-phenylalanine 1-methyl ester.

EXAMPLE 8

N-Neohexyl-α-Aspartame

Process C

To a methanol solution of L-aspartic acid β-t-butyl ester (1 mmol) in a Parr bottle, was added a solution of 3,3-dimethylbutyraldehyde (1 mmol) in methanol (30 mL), followed by addition of Pd/C (0.1 mmol). The mixture was hydrogenated at 50 psi at room temperature for 1 hr. If the reaction is not complete, fresh Pd/C may be added and hydrogenation continued. The mixture was filtered through a Celite® bed, and the bed washed with methanol. The filtrate and washings were combined, and the methanol removed under reduced pressure. The pH of the remaining aqueous solution was adjusted to 3 with concentrated hydrochloric acid. The precipitated solid was filtered and dried in a vacuum oven to give crude N-neohexyl-L-aspartic acid β-t-butyl ester hydrochloride. The crude product was slurried with aqueous ethanol and filtered to give pure N-neohexyl-L-aspartic acid β-t-butyl ester hydrochloride in 90% yield.

Benzotriazolyl-N-hydroxytris(dimethyamino) phosphonium hexafluorophosphate (BOP, 3.7 mmol) and triethyl amine (7.4 mmol) were added sequentially to a stirred solution of N-neohexyl-L-aspartic acid β-t-butyl ester (3.7 mmol) and phenylalanine methyl ester hydrochloride (3.7 mmol) in DMF/acetonitrile (15/20 mL) and the resulting reaction mixture was allowed to stir at room temperature overnight. Addition of brine (60 mL) resulted in instantaneous formation of a white precipitate. The resulting suspension was stirred for 2 hours and transferred to a separatory funnel. The aqueous phase was extracted ethyl acetate (1×200 mL, 2×50–80 mL). The combined ethyl acetate extracts were combined and washed successively with 1N HCl (2×100 mL), water (1×100 mL), saturated NaHCO$_3$ (2×100 mL), and brine (1×100 mL), dried over MgSO$_4$, filtered and evaporated to a light yellowish oil in quantitative yield. This oil was dissolved in ethyl acetate (30 mL) and treated with hydrochloric acid (4.3 M, 20 mL), with stirring, for 6 hrs. at room temperature. The pH of the mixture adjusted to 5.2 and transferred to a separatory funnel. The organic layer was separated. The aqueous layer was extracted with ethyl acetate (3×30 mL) and the combined ethyl acetate extracts were dried over anhydrous MgSO$_4$, filtered and evaporated to dryness. Crystallization of the crude product from 25% methanol- 75% water (30 mL) gave 2.5 g of pure N-[N-(3,3-dimethylbutyl)-L-α-aspartyl]-L-phenylalanine 1-methyl ester.

EXAMPLE 9

Enzymatic Synthesis of N-3,3-dimethylbutyl-L-aspartyl-L-phenylalanine methyl ester (Neotame)

Papain (180 mg) was added to a mixture of Mc Ilvaine buffer (pH 5.5) and ethanol (60%buffer/40%ethanol, total volume: 3 mL) containing mercaptoethanol (100 mmol), neohexyl-L-aspartic acid (200 mmol) and L-phenylalanine methyl ester (200 mmol). The mixture was agitated for 20 hours at room temperature. The reaction products may be separated by chromatography using ethyl acetate:methanol::hexane (60:30:10) as an eluent to provide pure α-neotame.

Other variations or modifications, which will be obvious to those skilled in the art, are within the scope and teachings of this invention. This invention is not to be limited except as set forth in the following claims.

We claim:

1. A compound represented by the formula

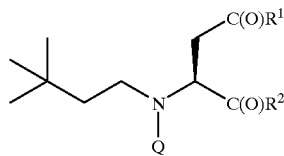

wherein R$^1$ and R$^2$ are independently hydroxy or alkoxy having 1 to 6 carbon atoms or together are oxygen, forming an anhydride thereof; and Q is hydrogen or (CH$_3$)$_3$C(CH$_2$)$_2$—.

2. A compound according to claim 1 wherein Q is hydrogen.

3. A compound according to claim 1, wherein R$^1$ and R$^2$ are hydroxy or methoxy.

4. The compound N-(3,3-dimethylbutyl)-L-aspartic acid.

5. The compound N,N-di-(3,3-dimethylbutyl)-L-aspartic acid.

6. The compound N-(3,3-dimethylbutyl)-L-aspartic anhydride.

7. A process for preparing N-(3,3-dimethylbutyl)-L-aspartic acid comprising the step of reductive alkylation of L-aspartic acid and 3,3-dimethylbutyraldehyde.

8. A process for preparing N-(3,3-dimethylbutyl)-L-aspartic acid or derivatives thereof represented by the formula

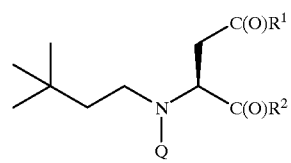

wherein R$^1$ and R$^2$ are independently hydroxy, lower alkoxy having 1 to 6 carbon atoms or together are oxygen, forming an anhydride, and Q is hydrogen or (CH$_3$)$_3$C(CH$_2$)$_2$—, said process comprising the step of reductive alkylation of

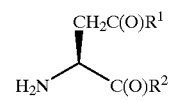

wherein R$^1$ and R$^2$ are as described above, with 3,3-dimethylbutyraldehyde.

9. A process according to claim 8 wherein the reductive alkylation is conducted using palladium on carbon in a hydrogen atmosphere with sodium bicarbonate.

10. A process according to claim 9, wherein Q is hydrogen.

11. A process according to claim 10, wherein R$^1$ and R$^2$ are hydroxy.

12. A process according to claim 10, where R$^1$ and R$^2$ are methoxy.

13. A process for preparing N-[N-(3,3-dimethylbutyl)-L-α-aspartyl]-L-phenylalanine 1-methyl ester comprising the steps of:

(a) condensing N-(3,3-dimethylbutyl)-L-aspartic anhydride with L-phenylalanine methyl ester to form a mixture of N-[N-(3,3-dimethylbutyl)-L-α-aspartyl]-L-phenylalanine 1-methyl ester and N-[N-(3,3-dimethylbutyl)-L-β-aspartyl]-L-phenylalanine 1-methyl ester; and (b) isolating said N-[N-(3,3-dimethylbutyl)-L-α-aspartyl]-L-phenylalanine 1-methyl ester from said mixture.

14. A process according to claim 13, further comprising the step of forming N-(3,3-dimethylbutyl)-L-aspartic anhydride by dehydration of an N-protected N-(3,3-dimethylbutyl) aspartic acid.

15. A process according to claim 14, wherein dehydration of the aspartic acid is conducted using acetic anhydride.

16. A process according to claim 14, wherein the N-protected N-(3,3-dimethylbutyl)-L-aspartic acid is N-formyl-N-(3,3-dimethyl-butyl)-L-aspartic acid, N-acetyl- N-(3,3-dimethylbutyl)-L-aspartic acid or N-benzyloxycarbonyl-N-(3,3-dimethylbutyl)-L-aspartic acid.

17. A process according to claim 13, wherein said step of isolating is by crystallization.

18. A process for preparing N-[N-(3,3-dimethylbutyl)-L-α-aspartyl]-L-phenylalanine 1-methyl ester comprising the steps of:
- (a) condensing N-(3,3-dimethylbutyl) aspartic anhydride with L-phenylalanine to form a mixture of α-L-phenylalanine N-neohexyl aspartic acid amide and β-L-phenylalanine N-neohexyl aspartic acid amide;
- (b) esterifying said amide mixture to form a mixture of N-[N-(3,3-dimethylbutyl)-L-α-aspartyl]-L-phenylalanine 1-methyl ester and N-[N-(3,3-dimethylbutyl)-L-β-aspartyl]-L-phenylalanine 1-methyl ester; and
- (c) isolating said N-[N-(3,3-dimethylbutyl)-L-α-aspartyl]-L-phenylalanine 1-methyl ester from said mixture.

19. A process according to claim 18, further comprising forming N-(3,3-dimethylbutyl)-L-aspartic anhydride by dehydration of an N-protected N-(3,3-dimethylbutyl) aspartic acid.

20. A process according to claim 19, wherein dehydration of the aspartic acid is conducted using acetic anhydride.

21. A process according to claim 19, wherein the N-protected N-(3,3-dimethylbutyl)-L-aspartic acid is N-formyl-N-(3,3-dimethyl-butyl)-L-aspartic acid, N-acetyl-N-(3,3-dimethylbutyl)-L-aspartic acid or N-benzyloxycarbonyl-N-(3,3-dimethylbutyl)-L-aspartic acid.

22. A process according to claim 18, wherein said step of isolating is by crystallization.

23. A process for preparing N-[N-(3,3-dimethylbutyl)-L-α-aspartyl]-L-phenylalanine 1-methyl ester comprising the steps of:
- (a) reducing a condensation product of 3,3-dimethylbutyraldehyde and β-protected L-aspartic acid to form a β-protected N-(3,3-dimethylbutyl)-L-aspartic acid;
- (b) forming a mixed anhydride of said β-protected N-(3,3-dimethylbutyl)-L-aspartic acid;
- (c) condensing said mixed anhydride with L-phenylalanine methyl ester to form a β-protected N-[N-(3,3-dimethylbutyl)-L-α-aspartyl]-L-phenylalanine 1-methyl ester; and
- (d) de-protecting said β-protected N-[N-(3,3-dimethylbutyl)-L-α-aspartyl]-L-phenylalanine 1-methyl ester to form N-[N-(3,3-dimethylbutyl)-L-α-aspartyl]-L-phenylalanine 1-methyl ester.

24. A process according to claim 23, further comprising crystallizing said N-[N-(3,3-dimethylbutyl)-L-α-aspartyl]-L-phenylalanine 1-methyl ester.

25. A process for preparing N-[N-(3,3-dimethylbutyl)-L-α-aspartyl]-L-phenylalanine 1-methyl ester comprising the steps of:
- (a) reducing a condensation product of 3,3-dimethylbutyraldehyde and β-protected L-aspartic acid to form a β-protected N-(3,3-dimethylbutyl)-L-aspartic acid;
- (b) condensing said β-protected N-(3,3-dimethylbutyl)-L-aspartic acid with an L-phenylalanine methyl ester to form a β-protected N-[N-(3,3-dimethylbutyl)-L-α-aspartyl]-L-phenylalanine 1-methyl ester; and
- (c) de-protecting said β-protected N-[N-(3,3-dimethylbutyl)-L-α-aspartyl]-L-phenylalanine 1-methyl ester to form N-[N-(3,3-dimethylbutyl)-L-α-aspartyl]-L-phenylalanine 1-methyl ester.

26. A process according to claim 25, wherein said L-phenylalanine ester is selected from the group consisting of L-phenylalanine methyl ester, L-phenylalanine methyl ester hydrochloride.

27. A process according to claim 25, further comprising crystallizing said N-[N-(3,3-dimethylbutyl)-L-α-aspartyl]-L-phenylalanine 1-methyl ester.

28. A process for preparing N-[N-(3,3-dimethylbutyl)-L-α-aspartyl]-L-phenylalanine 1-methyl ester comprising treating a mixture of a N-(3,3-dimethylbutyl)-L-aspartic acid and L-phenylalanine methyl ester with a protease enzyme to form N-[N-(3,3-dimethylbutyl)-L-α-aspartyl]-L-phenylalanine 1-methyl ester.

29. The process according to claim 28, wherein said protease enzyme is papain.

* * * * *

UNITED STATES PATENT AND TRADEMARK OFFICE
CERTIFICATE OF CORRECTION

PATENT NO.  : 6,077,962

DATED  : June 20, 2000

INVENTOR(S)  : INDRA PRAKASH ET AL.

It is certified that error appears in the above-identified patent and that said Letters Patent is hereby corrected as shown below:

<u>ON THE TITLE PAGE AT [54]</u>

The title should read --N-3,3-DIMETHYLBUTYL-L-α-ASPARTIC ACID AND ESTERS THEREOF, THE PROCESS OF PREPARING THE SAME, AND THE PROCESS FOR PREPARING N-[N-(3,3-DIMETHYLBUTYL)-L-α-ASPARTYL]-L-PHENYLALANINE 1-METHYL ESTER THEREFROM--.

<u>COLUMN 1</u>

Lines 1-7 should read --N-3,3-DIMETHYLBUTYL-L-α-ASPARTIC ACID AND ESTERS THEREOF, THE PROCESS OF PREPARING THE SAME, AND THE PROCESS FOR PREPARING N-[N-(3,3-DIMETHYLBUTYL)-L-α-ASPARTYL]-L-PHENYLALANINE 1-METHYL ESTER THEREFROM--.

<u>COLUMN 5</u>

Lines 10-16, " " should read

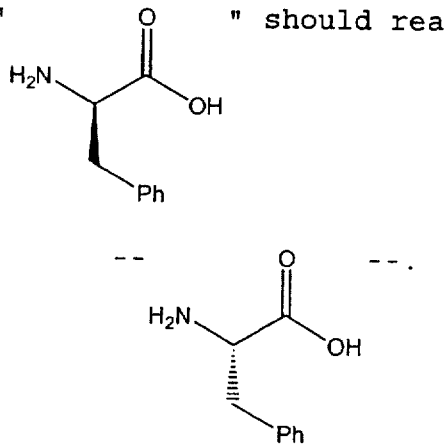

UNITED STATES PATENT AND TRADEMARK OFFICE
CERTIFICATE OF CORRECTION

PATENT NO. : 6,077,962

DATED : June 20, 2000

INVENTOR(S) : INDRA PRAKASH ET AL.

Page 2 of 3

It is certified that error appears in the above-identified patent and that said Letters Patent is hereby corrected as shown below:

COLUMN 6

Lines 21-27, " 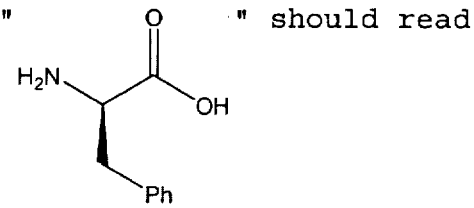 " should read

-- 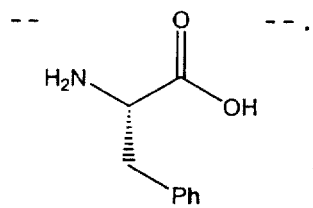 --.

COLUMN 9

Line 20, "β" should read --α--;

Lines 30-35, " 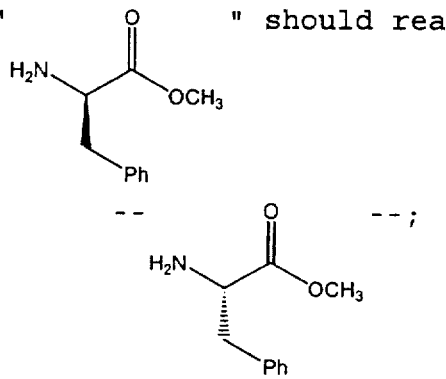 " should read

-- --;

UNITED STATES PATENT AND TRADEMARK OFFICE
CERTIFICATE OF CORRECTION

PATENT NO. : 6,077,962

DATED : June 20, 2000

INVENTOR(S) : INDRA PRAKASH ET AL.

It is certified that error appears in the above-identified patent and that said Letters Patent is hereby corrected as shown below:

Line 54, "β" should read --α--.

COLUMN 11

Line 22, "the a" should read --a--;
Line 40, "have be" should read --be--.

COLUMN 15

Line 14, "ethyl" should read --with ethyl--;
Line 15, "combined" should be deleted;
Line 23, "adjusted" should read --was adjusted--;
Line 34, "-L" should read -- -L-α--.

Signed and Sealed this

Twenty-second Day of May, 2001

Attest:

NICHOLAS P. GODICI

Attesting Officer

Acting Director of the United States Patent and Trademark Office